United States Patent
Singh et al.

(10) Patent No.: US 12,194,090 B2
(45) Date of Patent: Jan. 14, 2025

(54) TETANUS VACCINE PLATFORM FOR EMBEDDING COVID-19 VACCINE

(71) Applicant: PRIME BIO, INC., North Dartmouth, MA (US)

(72) Inventors: Bal Ram Singh, Dartmouth, MA (US); Kruti Patel, North Dartmouth, MA (US); Raj Kumar, Dartmouth, MA (US)

(73) Assignee: PRIME BIO, INC., North Dartmouth, MA (US)

( * ) Notice: Subject to any disclaimer, the term of this patent is extended or adjusted under 35 U.S.C. 154(b) by 0 days.

(21) Appl. No.: 18/060,401

(22) Filed: Nov. 30, 2022

(65) Prior Publication Data

US 2023/0201332 A1    Jun. 29, 2023

Related U.S. Application Data

(63) Continuation of application No. PCT/US2021/044054, filed on Jul. 30, 2021.

(60) Provisional application No. 63/032,544, filed on May 30, 2020.

(51) Int. Cl.
| | |
|---|---|
| A61K 39/02 | (2006.01) |
| A61K 39/215 | (2006.01) |
| A61K 39/39 | (2006.01) |
| A61P 31/14 | (2006.01) |
| A61K 39/00 | (2006.01) |

(52) U.S. Cl.
CPC ............ *A61K 39/215* (2013.01); *A61K 39/39* (2013.01); *A61P 31/14* (2018.01); *A61K 2039/542* (2013.01); *A61K 2039/55544* (2013.01); *A61K 2039/6037* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 1,104,009 | A | 7/1914 | Seguin |
| 6,699,966 | B1 | 3/2004 | Singh et al. |
| 11,040,090 | B2 | 6/2021 | Singh |
| 11,389,497 | B2 | 7/2022 | Singh et al. |
| 11,771,752 | B2 | 10/2023 | Singh |
| 2018/0014722 | A1 | 1/2018 | Lee et al. |
| 2018/0161406 | A1 | 6/2018 | Singh |
| 2019/0076518 | A1* | 3/2019 | Singh .................... A61P 31/04 |
| 2021/0121542 | A1 | 4/2021 | Singh et al. |
| 2021/0346292 | A1 | 11/2021 | Singh et al. |
| 2022/0288173 | A1 | 9/2022 | Singh et al. |
| 2022/0390461 | A1 | 12/2022 | Singh et al. |

FOREIGN PATENT DOCUMENTS

| | | | |
|---|---|---|---|
| WO | 2018/118974 | * | 6/2019 |
| WO | WO2019118974 A4 | | 10/2019 |
| WO | WO2021248145 A2 | | 12/2021 |

OTHER PUBLICATIONS

Zhao et al (Viral Immunol. 2006. 19(3): 518-524).*
Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol. Council. pp. 5-7).*
Thanh Le T, Andreadakis Z, Kumar A, Gomez Roman R, Tollefsen S, Saville M, Mayhew S. 2020. The COVID-19 vaccine development landscape. Nat Rev Drug Discov 19:305-306.
Hotez PJ, Bottazzi ME, Corry DB. 2020. The potential role of Th17 immune responses in coronavirus immunopathology and vaccine-induced immune enhancement. Microbes Infect doi:10.1016/j.micinf.2020.04.005.
Smatti MK, Al Thani AA, Yassine HM. 2018. Viral-Induced Enhanced Disease Illness. Front Microbiol 9:2991.
Konig MF, Powell MA, Staedtke V, Bai R-Y, Thomas DL, Fischer NM, Huq S, Khalafallah AM, Koenecke A, Xiong R, Mensh B, Papadopoulos N, Kinzler KW, Vogelstein B, Vogelstein JT, Athey S, Zhou S, Bettegowda C. 2020. Preventing cytokine storm syndrome in COVID-19 using α-1 adrenergic receptor antagonists. J Clin Invest doi:10.1172/jci139642.
Mehta P, McAuley DF, Brown M, Sanchez E, Tattersall RS, Manson JJ, Hlh Across Speciality Collaboration UK. 2020. COVID-19: consider cytokine storm syndromes and immunosuppression. Lancet 395:1033-1034.

(Continued)

*Primary Examiner* — Jennifer E Graser

(57) ABSTRACT

A recombinant SARS-CoV2 protein-based vaccine, and method of immunizing, is developed by either embedding the epitopes/domains, or chemically attaching, to an already established vaccine candidate, such as a detoxified recombinant tetanus neurotoxin (DrTeNT), to develop a novel vaccine to immunize against SARS-CoV2. The developed vaccine will have three novel contributions compared to the present vaccine technology; a) providing a novel and very effective vaccine platform; b) priming with DrTeNT will prepare the host immune system for better response; and c) oral delivery of the vaccine candidate with a group of neurotoxin binding proteins (NAPs) from *Clostridium* sp. A Detoxified recombinant tetanus neurotoxin (DrTeNT) is prepared by mutation of the active site amino acid residues is an effective vaccine candidate, and is to be used for embedding epitopes of SARS-CoV-2 virus protein for vaccination against Covid-19. DrTeNT is a risk-free vaccine, free of formalin or any other chemical adjuvants.

14 Claims, 6 Drawing Sheets
Specification includes a Sequence Listing.

(56) References Cited

OTHER PUBLICATIONS

Jose RJ, Manuel A. 2020. COVID-19 cytokine storm: the interplay between inflammation and coagulation. Lancet Respir Med.

Deinhardt K, Schiavo G. 2005. Endocytosis and retrograde axonal traffic in motor neurons. Biochem Soc Symp:139-50.

Schiavo G, Rossetto O, Santucci A, DasGupta BR, Montecucco C. 1992. Botulinum neurotoxins are zinc proteins. J Biol Chem 267:23479-83.

Lacy DB, Stevens RC. 1999. Sequence homology and structural analysis of the clostridial neurotoxins. J Mol Biol 291:1091-104.

Singh BR, Chang T-W, Kukreja R, Cai S. 2014. The Botulinum Neurotoxin Complex and the Role of Ancillary Proteins, p. 69-101. In Foster KA (ed), Molecular Aspects of Botulinum Neurotoxin. Springer New York, New York, NY.

Schiavo G, Matteoli M, Montecucco C. 2000. Neurotoxins affecting neuroexocytosis. Physiol Rev 80:717-66.

Ravichandran E, Janardhanan P, Patel K, Riding S, Cai S, Singh BR. 2016. In Vivo Toxicity and Immunological Characterization of Detoxified Recombinant Botulinum Neurotoxin Type A. Pharm Res 33:639-52.

Ghosal KJ, Patel K, Singh BR, Hale ML. 2018. Role of critical elements in botulinum neurotoxin complex in toxin routing across intestinal and bronchial barriers. PLoS One 13:e0199524.

PCT/US2021/044054 International Preliminary Report/Demand, forms 416, 409, mailed Jul. 25, 2022.

PCT/US2021/044054 International Search Report, form 220/210, mailed Jan. 21, 2022.

Williams GA, Koenen ME, Havenaar R, Wheeler P, Gowtage S, Lesellier S, Chambers MA. 2019. Survival of *Mycobacterium bovis* BCG oral vaccine during transit through a dynamic in vitro model simulating the upper gastrointestinal tract of badgers. PLoS One 14:e0214859.

Sanchez JL, Trofa AF, Taylor DN, Kuschner RA, DeFraites RF, Craig SC, Rao MR, Clemens JD, Svennerholm AM, Sadoff JC, et al. 1993. Safety and immunogenicity of the oral, whole cell/recombinant B subunit cholera vaccine in North American volunteers. J Infect Dis 167:1446-9.

Kumar R, Chang, T. W., and Singh, B. R. 2017. Evolutionary traits of toxins. Springer Netherlands.

Singh BR, Li B, Read D. 1995. Botulinum versus tetanus neurotoxins: why is botulinum neurotoxin but not tetanus neurotoxin a food poison? Toxicon 33:1541-7.

Yang W, Lindo P, Riding S, Chang TW, Cai S, Van T, Kukreja R, Zhou Y, Vasa K, Singh BR. 2008. Expression, purification and comparative characterisation of enzymatically deactivated recombinant botulinum neurotoxin type A. The Botulinum journal 1:219-241.

Sakaguchi G. 1983. Clostridium botulinum toxins. Pharmacol Ther 19:165-94.

Costantino HR, Schwendeman SP, Griebenow K, Klibanov AM, Langer R. 1996. The secondary structure and aggregation of lyophilized tetanus toxoid. J Pharm Sci 85:1290-3.

Belouzard S, Millet JK, Licitra BN, Whittaker GR. 2012. Mechanisms of coronavirus cell entry mediated by the viral spike protein. Viruses 4:1011-33.

Wrapp D, Wang N, Corbett KS, Goldsmith JA, Hsieh CL, Abiona O, Graham BS, McLellan JS. 2020. Cryo-EM structure of the 2019-nCoV spike in the prefusion conformation. Science 367:1260-1263.

Matsuyama S, Ujike M, Morikawa S, Tashiro M, Taguchi F. 2005. Protease-mediated enhancement of severe acute respiratory syndrome coronavirus infection. Proc Natl Acad Sci U S A 102:12543-7.

Robson B. 2020. COVID-19 Coronavirus spike protein analysis for synthetic vaccines, a peptidomimetic antagonist, and therapeutic drugs, and analysis of a proposed achilles' heel conserved region to minimize probability of escape mutations and drug resistance. Comput Biol Med doi:10.1016/j.compbiomed.2020.103749:103749.

Robson B. 2020. Computers and viral diseases. Preliminary bioinformatics studies on the design of a synthetic vaccine and a preventative peptidomimetic antagonist against the SARS-COV-2 (2019-nCOV, COVID-19) coronavirus. Comput Biol Med 119:103670.

Grifoni A, Sidney J, Zhang Y, Scheuermann RH, Peters B, Sette A. 2020. Candidate targets for immune responses to 2019-Novel Coronavirus (nCoV): sequence homology- and bioinformatic-based predictions.

Ahmed SF, Quadeer AA, McKay MR. 2020. Preliminary Identification of Potential Vaccine Targets for the COVID-19 Coronavirus (SARS-CoV-2) Based on SARS-CoV Immunological Studies. Viruses 12.

Shang J, Ye G, Shi K, Wan Y, Luo C, Aihara H, Geng Q, Auerbach A, Li F. 2020. Structural basis of receptor recognition by SARS-CoV-2.

Yan R, Zhang Y, Li Y, Xia L, Guo Y, Zhou Q. 2020. Structural basis for the recognition of SARS-CoV-2 by full-length human ACE2. Science 367:1444-1448.

Yao B, Zhang L, Liang S, Zhang C. 2012. SVMTriP: a method to predict antigenic epitopes using support vector machine to integrate tri-peptide similarity and propensity. PLoS One 7:e45152.

Zhao et al., 2006. "Immunization of Mice with a DNA Vaccine Based on Severe Acute Respiratory Syndrome Coronavirus Spike Protein Fragment 1", Viral Immunology. vol. 19. No. 3, pp. 518-524.

KB Patel, S Cai, M Adler, B K. Singh, V S. Parmar, BR Singh, Nov. 2018, "Natural Compounds and Their Analogues as Potent Antidotes against the Most Poisonous Bacterial Toxin", Applied and Environmental Microbiology. vol. 84, No. 24, pp. 1-15.

R Kukreja, BR Singh, "The botulinum toxin as a therapeutic agent: molecular and pharmacological insights". .2015. Research and Reports in Biochemistry. Vo. 5, pp. 173-183.

\* cited by examiner

FIG. 1

SEQUENCE LISTING

```
Sequence total quantity: 46
SEQ ID NO: 1            moltype = AA  length = 1273
FEATURE                 Location/Qualifiers
source                  1..1273
                        mol_type = protein
                        organism = SARS CoV-2
SEQUENCE: 1
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                   1273

SEQ ID NO: 2            moltype = AA  length = 229
FEATURE                 Location/Qualifiers
source                  1..229
                        mol_type = protein
                        organism = SARS-CoV2
SEQUENCE: 2
RVQPTESIVR FPNITNLCPF GEVFNATRFA SVYAWNRKRI SNCVADYSVL YNSASFSTFK   60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
```

```
PTNGVGYQPY RVVVLSFELL HAPATVCGPK KSTNLVKNKC VNFHHHHHH              229

SEQ ID NO: 3              moltype = AA   length = 19
FEATURE                   Location/Qualifiers
source                    1..19
                          mol_type = protein
                          organism = SARS-CoV2
SEQUENCE: 3
PSKRSFIELD LLFNKVTLA                                              19

SEQ ID NO: 4              moltype = AA   length = 25
FEATURE                   Location/Qualifiers
source                    1..25
                          mol_type = protein
                          organism = SARS-CoV2
SEQUENCE: 4
NGVEGFNCYF PLQSYGFQPT NGVGY                                       25

SEQ ID NO: 5              moltype = AA   length = 18
FEATURE                   Location/Qualifiers
source                    1..18
                          mol_type = protein
                          organism = SARS-CoV2
SEQUENCE: 5
TESNKKFLPQ QFGRDIAG                                               18

SEQ ID NO: 6              moltype = AA   length = 1604
FEATURE                   Location/Qualifiers
source                    1..1604
                          mol_type = protein
                          organism = SARS-CoV2
SEQUENCE: 6
MKGKPSKRSF IEDLLFNKVT LAGGTESNKK FLPFQQFGRD IAGPITINNF RYSDPVNNDT  60
IIMMEPPYCK GLDIYYKAFK ITDRIWIVPE RYEFGTKPED FNPPSSLIEG ASEYYDPNYL  120
RTDSDKDRFL QTMVKLFNRI KNNVAGEALL DKIINAIPYL GNSYSLLDKF DTNSNSVSFN  180
LLEQDPSGAT TKSAMLTNLI IFGPGPVLNK NEVRGIVLRV DNKNYFPCRD GFGSIMQMAF  240
CPEYVPTFDN VIENITSLTI GKSKYFQDPA LLLMHALIHV LHGLYGMQVS SHEGPSKRSF  300
IEDLLFNKVT LAGGTESNKK FLPFQQFGRD IAGIIPSKQE IYMQHTYPIS AEALFTFGGQ  360
DANLISIDIK NDLYEKTLND YKAIANKLSQ VTSCNDPNID IDSYKQIYQQ KYQFDKDSNG  420
QYIVNEDKFQ ILYNSIMYGF TEIELGKKFN IKTRLSYFSM NHDPVKIPNL LDDTIYNDTE  480
GFNIESKDLK SEYKGQNMRV NTNAFRNVDG SGLVSKLIGL CKKIIPPTNI REGPSKRSFI  540
EDLLFNKVTL AGGTESNKKF LPFQQFGRDI AGNLYNRTAS LTDLGGELCI KIKNEDLTFI  600
AEKNSFSEEP FQDEIVSYNT KNKPLNFNYS LDKIILDYNL QSKITLPNDR TTPVTKGIPY  660
APEYKSNAAS TIEIHNIDDN TIYQYLYAQK SPTTLQRITM TNSVDDALIN STKIYSYFPS  720
VISKVNQGAQ GPSKRSFIED LLFNKVTLAG GTESNKKFLP FQQFGRDIAG GILFLQWVRD  780
IIDDFTNESS QKTTIDKISD VSTIVPYIGP ALNIVKQGYE GNFIGALETT GVVLLLEYIP  840
EITLPVIAAL SIAESSTGPS KRSFIEDLLF NKVTLAGGTE SNKKFLPFQQ FGRDIAGQKE  900
KIIKTIDNFL EKRYEKWIEV YKLVKAKWLG TVNTQFQKRS YQMYRSLEYQ VDAIKKIIDY  960
EYKIYSGPDG PSKRSFIEDL LFNKVTLAGG TESNKKFLPF QQFGRDIAGK EQIADEINNL  1020
KNKLEEKANK AMININIFMR ESSRSFLVNQ MINEAKKQLL EFDTQSKNIL MQYIKANSKF  1080
IGITELKKLE SKINKVFSTP IPFSYSKNLD CWVDNEEDID VILKKSTILN LDINNDIISD  1140
ISGFNSSVIT YPDAQLVPGI NGKAIHLVNN ESSEVIVHKA MDIEYNDMFN NFTVSFWLRV  1200
PKVSASHLEQ YGTNEYSIIS SMKKYSLSIG SGWSVSLKGN NLIWTLKDSA GEVRQITFRD  1260
LSDKFNAYLA NKWVFITITN DRLSSANLYI NGVLMGSAEI TGLGAIREDN NITLKLDRCN  1320
NNNQYVSIDK FRIFCKALNP KEIEKLYTSY LSITFLRDFW GNPLRYDTEY YLIPVASSSK  1380
DVQLKNITDY MYLTNAPSYT NGKLNIYYRR LYNGLKFIIK RYTPNNEIDS FVKSGDFIKL  1440
YVSYNNNEHI VGYPKDGNAF NNLDRILRVG YNAPGIPLYK KMEAVKLRDL KTYSVQLKLY  1500
DDKNASLGLV GTHNGQIGND PNRDILIASN WYFNHLKDKI LGCDWYFVPT DEGWTNDGPS  1560
KRSFIEDLLF NKVTLAGGTE SNKKFLPFQQ FGRDIAGGHH HHHH                  1604

SEQ ID NO: 7              moltype = AA   length = 1604
FEATURE                   Location/Qualifiers
source                    1..1604
                          mol_type = protein
                          organism = SARS CoV-2
SEQUENCE: 7
MKGKPSKRSF IEDLLFNKVT LAGGTESNKK FLPFQQFGRD IAGPITINNF RYSDPVNNDT  60
IIMMEPPYCK GLDIYYKAFK ITDRIWIVPE RYEFGTKPED FNPPSSLIEG ASEYYDPNYL  120
RTDSDKDRFL QTMVKLFNRI KNNVAGEALL DKIINAIPYL GNSYSLLDKF DTNSNSVSFN  180
LLEQDPSGAT TKSAMLTNLI IFGPGPVLNK NEVRGIVLRV DNKNYFPCRD GFGSIMQMAF  240
CPEYVPTFDN VIENITSLTI GKSKYFQDPA LLLMHALIHV LHGLYGMQVS SHEGPSKRSF  300
IEDLLFNKVT LAGGTESNKK FLPFQQFGRD IAGIIPSKQE IYMQHTYPIS AEALFTFGGQ  360
DANLISIDIK NDLYEKTLND YKAIANKLSQ VTSCNDPNID IDSYKQIYQQ KYQFDKDSNG  420
QYIVNEDKFQ ILYNSIMYGF TEIELGKKFN IKTRLSYFSM NHDPVKIPNL LDDTIYNDTE  480
GFNIESKDLK SEYKGQNMRV NTNAFRNVDG SGLVSKLIGL CKKIIPPTNI REGPSKRSFI  540
EDLLFNKVTL AGGTESNKKF LPFQQFGRDI AGNLYNRTAS LTDLGGELCI KIKNEDLTFI  600
AEKNSFSEEP FQDEIVSYNT KNKPLNFNYS LDKIILDYNL QSKITLPNDR TTPVTKGIPY  660
APEYKSNAAS TIEIHNIDDN TIYQYLYAQK SPTTLQRITM TNSVDDALIN STKIYSYFPS  720
VISKVNQGAQ GPSKRSFIED LLFNKVTLAG GTESNKKFLP FQQFGRDIAG GILFLQWVRD  780
```

```
IIDDFTNESS QKTTIDKISD VSTIVPYIGP ALNIVKQGYE GNFIGALETT GVVLLLEYIP   840
EITLPVIAAL SIAESSTGPS KRSFIEDLLF NKVTLAGGTE SNKKFLPFQQ FGRDIAGQKE   900
KIIKTIDNFL EKRYEKWIEV YKLVKAKWLG TVNTQFQKRS YQMYRSLEYQ VDAIKKIIDY   960
EYKIYSGPDG PSKRSFIEDL LFNKVTLAGG TESNKKFLPF QQFGRDIAGK EQIADEINNL  1020
KNKLEEKANK AMININIFMR ESSRSFLVNQ MINEAKKQLL EFDTQSKNIL MQYIKANSKF  1080
IGITELKKLE SKINKVFSTP IPFSYSKNLD CWVDNEEDID VILKKSTILN LDINNDIISD  1140
ISGFNSSVIT YPDAQLVPGI NGKAIHLVNN ESSEVIVHKA MDIEYNDMFN NFTVSFWLRV  1200
PKVSASHLEQ YGTNEYSIIS SMKKYSLSIG SGWSVSLKGN NLIWTLKDSA GEVRQITFRD  1260
LSDKFNAYLA NKWVFITITN DRLSSANLYI NGVLMGSAEI TGLGAIREDN NITLKLDRCN  1320
NNNQYVSIDK FRIFCKALNP KEIEKLYTSY LSITFLRDFW GNPLRYDTEY YLIPVASSSK  1380
DVQLKNITDY MYLTNAPSYT NGKLNIYYRR LYNGLKFIIK RYTPNNEIDS FVKSGDFIKL  1440
YVSYNNNEHI VGYPKDGNAF NNLDRILRVG YNAPGIPLYK KMEAVKLRDL KTYSVQLKLY  1500
DDKNASLGLV GTHNGQIGND PNRDILIASN WYFNHLKDKI LGCDWYFVPT DEGWTNDGPS  1560
KRSFIEDLLF NKVTLAGGTE SNKKFLPFQQ FGRDIAGGHH HHHH                   1604

SEQ ID NO: 8            moltype = AA   length = 20
FEATURE                 Location/Qualifiers
source                  1..20
                        mol_type = protein
                        organism = SARS-CoV2
SEQUENCE: 8
LNEVAKNLNE SLIDLQELGK                                               20

SEQ ID NO: 9            moltype = AA   length = 20
FEATURE                 Location/Qualifiers
source                  1..20
                        mol_type = protein
                        organism = SARS CoV-2
SEQUENCE: 9
TLVKQLSSNF GAISSVLNDI                                               20

SEQ ID NO: 10           moltype = AA   length = 20
FEATURE                 Location/Qualifiers
source                  1..20
                        mol_type = protein
                        organism = SARS CoV-2
SEQUENCE: 10
QQLIRAAEIR ASANLAATKM                                               20

SEQ ID NO: 11           moltype = AA   length = 20
FEATURE                 Location/Qualifiers
source                  1..20
                        mol_type = protein
                        organism = SARS CoV-2
SEQUENCE: 11
KEELDKYFKN HTSPDVDLGD                                               20

SEQ ID NO: 12           moltype = AA   length = 20
FEATURE                 Location/Qualifiers
source                  1..20
                        mol_type = protein
                        organism = SARS CoV-2
SEQUENCE: 12
VMVTIMLCCM TSCCSCLKGC                                               20

SEQ ID NO: 13           moltype = AA   length = 20
FEATURE                 Location/Qualifiers
source                  1..20
                        mol_type = protein
                        organism = SARS CoV-2
SEQUENCE: 13
MYICGDSTEC SNLLLQYGSF                                               20

SEQ ID NO: 14           moltype = AA   length = 20
FEATURE                 Location/Qualifiers
source                  1..20
                        mol_type = protein
                        organism = SARS CoV-2
SEQUENCE: 14
ITSGWTFGAG AALQIPFAMQ                                               20

SEQ ID NO: 15           moltype = AA   length = 20
FEATURE                 Location/Qualifiers
source                  1..20
                        mol_type = protein
                        organism = SARS CoV-2
SEQUENCE: 15
QSIIAYTMSL GAENSVAYSN                                               20
```

```
SEQ ID NO: 16           moltype = AA    length = 20
FEATURE                 Location/Qualifiers
source                  1..20
                        mol_type = protein
                        organism = SARS CoV-2
SEQUENCE: 16
DTTDAVRDPQ TLEILDITPC                                              20

SEQ ID NO: 17           moltype = AA    length = 20
FEATURE                 Location/Qualifiers
source                  1..20
                        mol_type = protein
                        organism = SARS CoV-2
SEQUENCE: 17
VSVITPGTNT SNQVAVLYQD                                              20

SEQ ID NO: 18           moltype = AA    length = 20
FEATURE                 Location/Qualifiers
source                  1..20
                        mol_type = protein
                        organism = SARS CoV-2
SEQUENCE: 18
QQQQGQTVTK KSAAEASKKP                                              20

SEQ ID NO: 19           moltype = AA    length = 20
FEATURE                 Location/Qualifiers
source                  1..20
                        mol_type = protein
                        organism = SARS CoV-2
SEQUENCE: 19
RRGPEQTQGN FGDQELIRQG                                              20

SEQ ID NO: 20           moltype = AA    length = 20
FEATURE                 Location/Qualifiers
source                  1..20
                        mol_type = protein
                        organism = SARS CoV-2
SEQUENCE: 20
AALALLLLDR LNQLESKMSG                                              20

SEQ ID NO: 21           moltype = AA    length = 20
FEATURE                 Location/Qualifiers
source                  1..20
                        mol_type = protein
                        organism = SARS CoV-2
SEQUENCE: 21
SSSRSRNSSR NSTPGSSRGT                                              20

SEQ ID NO: 22           moltype = AA    length = 20
FEATURE                 Location/Qualifiers
source                  1..20
                        mol_type = protein
                        organism = SARS CoV-2
SEQUENCE: 22
AYKTFPPTEP KKDKKKKADE                                              20

SEQ ID NO: 23           moltype = AA    length = 20
FEATURE                 Location/Qualifiers
source                  1..20
                        mol_type = protein
                        organism = SARS CoV-2
SEQUENCE: 23
YTGAIKLDDK DPNFKDQVIL                                              20

SEQ ID NO: 24           moltype = AA    length = 20
FEATURE                 Location/Qualifiers
source                  1..20
                        mol_type = protein
                        organism = SARS CoV-2
SEQUENCE: 24
INTNSSPDDQ IGYYRRATRR                                              20

SEQ ID NO: 25           moltype = AA    length = 20
FEATURE                 Location/Qualifiers
source                  1..20
                        mol_type = protein
                        organism = SARS CoV-2
SEQUENCE: 25
DGIIWVATEG ALNTPKDHIG                                              20
```

```
SEQ ID NO: 26            moltype = AA   length = 20
FEATURE                  Location/Qualifiers
source                   1..20
                         mol_type = protein
                         organism = SARS CoV-2
SEQUENCE: 26
NGERSGARSK QRRPQGLPNN                                                      20

SEQ ID NO: 27            moltype = AA   length = 20
FEATURE                  Location/Qualifiers
source                   1..20
                         mol_type = protein
                         organism = SARS CoV-2
SEQUENCE: 27
QIAQFAPSAS AFFGMSRIGM                                                      20

SEQ ID NO: 28            moltype = AA   length = 20
FEATURE                  Location/Qualifiers
source                   1..20
                         mol_type = protein
                         organism = SARS CoV-2
SEQUENCE: 28
FIASFRLFAR TRSMWSFNPE                                                      20

SEQ ID NO: 29            moltype = AA   length = 20
FEATURE                  Location/Qualifiers
source                   1..20
                         mol_type = protein
                         organism = SARS CoV-2
SEQUENCE: 29
IAGHHLGRCD IKDLPKEITV                                                      20

SEQ ID NO: 30            moltype = AA   length = 20
FEATURE                  Location/Qualifiers
source                   1..20
                         mol_type = protein
                         organism = SARS CoV-2
SEQUENCE: 30
VATLQAENVT GLFKDCSKVI                                                      20

SEQ ID NO: 31            moltype = AA   length = 20
FEATURE                  Location/Qualifiers
source                   1..20
                         mol_type = protein
                         organism = SARS CoV-2
SEQUENCE: 31
VHVMSKHTDF SSEIIGYKAI                                                      20

SEQ ID NO: 32            moltype = AA   length = 20
FEATURE                  Location/Qualifiers
source                   1..20
                         mol_type = protein
                         organism = SARS CoV-2
SEQUENCE: 32
AVANGDSEVV LKKLKKSLNV                                                      20

SEQ ID NO: 33            moltype = AA   length = 20
FEATURE                  Location/Qualifiers
source                   1..20
                         mol_type = protein
                         organism = SARS CoV-2
SEQUENCE: 33
DGISQYSLRL IDAMMFTSDL                                                      20

SEQ ID NO: 34            moltype = AA   length = 20
FEATURE                  Location/Qualifiers
source                   1..20
                         mol_type = protein
                         organism = SARS CoV-2
SEQUENCE: 34
VEKKKLDGFM GRIRSVYPVA                                                      20

SEQ ID NO: 35            moltype = AA   length = 20
FEATURE                  Location/Qualifiers
source                   1..20
                         mol_type = protein
                         organism = SARS CoV-2
SEQUENCE: 35
```

QYIRKLHDEL TGHMLDMYSV                                                                                      20

SEQ ID NO: 36           moltype = AA   length = 20
FEATURE                 Location/Qualifiers
source                  1..20
                        mol_type = protein
                        organism = SARS CoV-2
SEQUENCE: 36
AKVTSAMQTM LFTMLRKLDN                                                                                      20

SEQ ID NO: 37           moltype = AA   length = 20
FEATURE                 Location/Qualifiers
source                  1..20
                        mol_type = protein
                        organism = SARS CoV-2
SEQUENCE: 37
ATNYDLSVVN ARLRAKHYVY                                                                                      20

SEQ ID NO: 38           moltype = AA   length = 20
FEATURE                 Location/Qualifiers
source                  1..20
                        mol_type = protein
                        organism = SARS CoV-2
SEQUENCE: 38
LIGEAVKTQF NYYKKVDGVV                                                                                      20

SEQ ID NO: 39           moltype = AA   length = 20
FEATURE                 Location/Qualifiers
source                  1..20
                        mol_type = protein
                        organism = SARS CoV-2
SEQUENCE: 39
MPNMLRIMAS LVLARKHTTC                                                                                      20

SEQ ID NO: 40           moltype = AA   length = 20
FEATURE                 Location/Qualifiers
source                  1..20
                        mol_type = protein
                        organism = SARS CoV-2
SEQUENCE: 40
YQIGGYTEKW ESGVKDCVVL                                                                                      20

SEQ ID NO: 41           moltype = AA   length = 20
FEATURE                 Location/Qualifiers
source                  1..20
                        mol_type = protein
                        organism = SARS CoV-2
SEQUENCE: 41
TPSDFVRATA TIPIQASLPF                                                                                      20

SEQ ID NO: 42           moltype = AA   length = 20
FEATURE                 Location/Qualifiers
source                  1..20
                        mol_type = protein
                        organism = SARS CoV-2
SEQUENCE: 42
LLYDANYFLC WHTNCYDYCI                                                                                      20

SEQ ID NO: 43           moltype = AA   length = 20
FEATURE                 Location/Qualifiers
source                  1..20
                        mol_type = protein
                        organism = SARS CoV-2
SEQUENCE: 43
GVKHVYQLRA RSVSPKLFIR                                                                                      20

SEQ ID NO: 44           moltype = AA   length = 20
FEATURE                 Location/Qualifiers
source                  1..20
                        mol_type = protein
                        organism = SARS CoV-2
SEQUENCE: 44
TCELYHYQEC VRGTTVLLKE                                                                                      20

SEQ ID NO: 45           moltype = AA   length = 20
FEATURE                 Location/Qualifiers
source                  1..20
                        mol_type = protein
                        organism = SARS CoV-2

```
SEQUENCE: 45
FYSKWYIRVG ARKSAPLIEL                                               20

SEQ ID NO: 46           moltype = AA   length = 20
FEATURE                 Location/Qualifiers
source                  1..20
                        mol_type = protein
                        organism = SARS CoV-2
SEQUENCE: 46
LVVRCSFYED FLEYHDVRVV                                               20
```

TETANUS VACCINE PLATFORM FOR EMBEDDING COVID-19 VACCINE

CROSS-REFERENCE TO RELATED APPLICATIONS

The present application is a continuation-in-part of PCT/US2021/044054, entitled "Tetanus Vaccine Platform for Embedding Covid-19 Vaccine" that was filed on Jul. 30, 2021, and which claims priority to U.S. Provisional Ser. No. 63/032,544 entitled "Tetanus Vaccine Platform for Embedding Covid-19 Vaccine that was filed on May 30, 2020; the contents of all of which are incorporated herein by reference, in their entirety.

SEQUENCE LISTING

The specification further incorporates by reference the Sequence Listing submitted herewith via EFS on Nov. 30, 2022. Pursuant to 37 C.F.R. § 1.52(c)(5), the Sequence Listing text file, identified as 45,000 bytes and was created on Nov. 30, 2022 with file name: "000410uscp_Sequence-Listing.xml", Sequences: 46, File size: 45 kb. The entire contents of the Sequence Listing are hereby incorporated by reference. The Sequence Listing does not extend beyond the scope of the specification and thus does not contain new matter.

FIELD OF THE INVENTION

The present invention relates generally to protein or nucleic acid based COVID-19 vaccines; and more particularly to a pre-used tetanus vaccine vehicle to directly activate memory cells for the processing of the vaccine, without necessarily alerting the entire immune system for any dire immune response.

BACKGROUND OF THE INVENTION

The corona virus like SARS (Severe Acute Respiratory Syndrome) and MERS (Middle East Respiratory syndrome) causes lethal infections in the humans. The most recent of the Corona viruses is SARS-CoV-2 (CoV-2), also known as 2019-nCoV, that started spreading from Wuhan, China, and has spread across the globe starting from late 2019. Several recent animal studies for SARS-CoV-2 vaccines had identified two potential safety issues: cellular immunopathology and antibody-dependent enhancement (ADE), which have proven that the delivery platforms and adjuvants play very important roles in the host responses to the immunopathology in the host (1, 2). In the 1960s, the formalin-inactivated respiratory syncytial virus (RSV) vaccine caused immune-enhanced disease that may be due to the ADE (3).

An infection by viruses like SARS-CoV-2 triggers several mechanisms of host immune responses, such as innate, cell-mediated, and adoptive. Depending on the immune status of the host and that of the preponderance of the virions, then these immune responses could mitigate the infection by clearing up the virus, and manage the infection at a suboptimal level to develop long term memory cells for future immune responses to a subsequent infection situation, and/or try to overwhelm the virus by the all-out dire immune response to neutralize the virus in plasma, as well as in the infected cells (1, 2). The latter is managed by what is termed a cytokine storm, which leads to the damage not only the virus infected cells, but also to normal cells, leading complications for the patients aggravating the conditions which often results in death (4-6).

All the current vaccine efforts either use the whole viral protein, or a corresponding DNA/RNA based vaccine that is to be delivered by a variety of means, such as viral vector, nanoparticles, or lipid vesicles (1). These approaches and vehicles continue to pose the problem of dire immune response mediated by cytokine storm. Part of the problem with the -COVID-19 virus is its high virulent nature, which allows it to sneak into cells.

None of these approaches use a pre-used vaccine vehicle. The advantage of pre-used vaccine vehicles would be to directly activate memory cells for the processing of the vaccine, without necessarily alerting the entire immune system for any dire immune response. At the same time, the antigen presenting cells (APCs) will be able to process the epitopes derived from the S and N proteins of SARS-CoV-2, which would allow more effective and perhaps faster immune response.

Tetanus Vaccines

Tetanus is often a fatal disease caused by tetanus neurotoxin (TeNT) produced by *Clostridium tetani*, which can infect wounds resulting from general cuts, needle use, and unhygienic birth practices. The tetanus vaccination has become common throughout the world at least during infant ages. One hundred percent tetanus immunization is needed for the world population, as this is a disease, which often turns fatal. In addition, there is a need for booster shots of tetanus every 10 years, which frequently is overlooked. At present there are over 200,000 annual tetanus deaths (mostly maternal and neonatal) worldwide which could be prevented with effective immunization. For all practical purposes the world's entire population is immunized with tetanus vaccine, making a tetanus-based delivery of CoV-2 vaccine a safe proposition.

The production of tetanus toxoid vaccine by chemical inactivation of tetanus toxin with formaldehyde has remained virtually unchanged since it was first introduced in the 1920, which requires administration of toxoid vaccine injection by trained medical staff. It is required to improve the vaccine in terms of delivering the vaccine without needles. Moreover, injectable vaccines have chances for secondary infection due to needles, and require medically trained person to inject the vaccine. It has also reported that formaldehyde can cause allergic reactions which includes >8 cm of erythema or induration, sore and swollen arm, and systemic manifestation such as fever and malaise reported in several studies (7-10). The method is inconvenient and frightening for many people, especially children. It has been reported altogether, 24% of parents and 63% of children reported a fear of needles. Needle fear was the primary reason for immunization non-compliance for 7% and 8% of parents and children, respectively (11).

Moreover, upon intramuscular injection for the patients, local reactions consisting of pain, erythema, tenderness and indurations at the injection site are common, and are usually associated with systemic reactions including transient fever and irritability. The reactions are due to the formaldehyde present in the formulation, which causes adverse effects upon injection.

What is needed within the vaccine industry is a vaccine composition comprising a detoxified tetanus neurotoxin (TeNT) and epitopes of the targeted pathogen, wherein the vaccine composition does not comprise formaldehyde.

SUMMARY OF THE INVENTION

Various embodiments of the present invention comprise a detoxified form of whole tetanus neurotoxin (TeNT) containing at least one mutated light chain and native heavy chain, which can be used alone as a protein or nucleic acid vaccine for subcutaneous or intramuscular administration; or in combination with the neurotoxin associated proteins (NAPs), including NBP (Neurotoxin Binding Protein) or any of the hemagglutinin units or ORFs (open reading frames) or P80 for oral/sublingual and intranasal delivery. This recombinant vaccine candidate (detoxified recombinant TeNT or DrTeNT proteins) is a major advancement for the SARS-CoV-2 vaccine, especially as it can be combined with immunogenic recombinant fragments of corona epitopes.

In an embodiment, the present invention employs the use of neurotoxin associated proteins (NAPs) of botulinum neurotoxin (BoNT) produced by *Clostridium botulinum* as delivery vehicles (e.g. adjuvants or carrier or protectant or bioenhancer) of the vaccine for oral/sublingual, and/or intranasal administration.

The present invention further comprises a mutated recombinant vaccine composition, and method of use to immunize, comprising one or more detoxified forms of a whole or part of a tetanus neurotoxin (DrTeNT) proteins, and one or more epitopes derived from a toxin, a pathogen, or a disease, wherein the vaccine composition is able to immunize a human or a non-human mammal against the toxin, the pathogen, or the disease, which are derived from animals, plants, fungi, bacteria, or viruses. And the epitopes are derived from one or more diseases comprising, by way of non-limiting examples: tuberculosis, malaria, cancer, flu, pneumonia, psoriasis, itch, and lime disease.

In one or more embodiments, the vaccine composition comprises a detoxified form of the whole or the part of the tetanus neurotoxin (DrTeNT) with at least one mutated light chain and at least one native heavy chain; and/or with the DrTeNT as a carrier protein and one or more epitopes or subunits of the SARS-CoV-2 virus; and/or a hybrid protein linking a receptor-binding domain (RBD) epitope or embedded in the amino acid sequence of DrTeNT CoV2 to produce a vaccine platform (DrTeNT-CoV2 protein); protein; and/or comprising a S1 subunit (or other subunit) of a SARS-CoV spike (S) protein comprising a receptor-binding domain (RBD) epitope.

In one or more embodiments, the vaccine composition comprises a detoxified form of whole or the part of the detoxified recombinant tetanus neurotoxin (DrTeNT) attach either covalently or non-covalently to S1 (SEQ ID NO: 1) or RBD of SARS-COV2 (SEQ ID NO: 2).

In one or more embodiments, the vaccine compositions of the present invention further comprise a formulation comprising one or more neurotoxin associated proteins (NAPs) derived from a botulinum neurotoxin (BoNT) produced by a *Clostridium botulinum*.

In one or more embodiments, the vaccine compositions of the present invention further comprises above formulation with or without alum, polylactic acid, polyglycolic acid, Vitamin E, and colloidal particle.

In one or more embodiments, the vaccine compositions of the present invention epitopes with at least 95% sequence identity one or more of SEQ ID NOS: 9-45; and/or at least 85% sequence identity to SEQ ID NOS: 1-8.

In one or more embodiments, the present invention further comprises a recombinant TeNT or DrTeNT vector comprising a nucleic acid that encodes a polypeptide comprising a DrTeNT protein; and a promoter which is operably linked to said polynucleotide. The vector further comprises a nucleic acid encoding one or more epitopes of a toxin, a pathogen or derived from a disease. In an embodiment, the epitopes are derived from or directed against Covid-19, e.g. encoding a SARS-CoV receptor binding domain (RBD) gene and a DrTeNT-CoV2 gene to express a RBD and DrTeNT-CoV2 hybrid protein (DrTeNT-CoV2 protein).

In one or more embodiments, the present invention further comprises a construct which includes one or more epitopes embedded or attached covalently to a DrTeNT amino acid or nucleotide sequence.

In one or more embodiments, the present invention further comprises a construct which includes either S1/RBD embedded or covalently/non-covalently attached to the DrTeNT amino acid/nucleotide sequence.

In one or more embodiments, the present invention further comprises a priming step with: DrTeNT; or a related tetanus; or any other vaccines (tuberculosis, malaria, cancer, flu, dengue, pneumonia, psoriasis, itch, HIV, and Lyme disease) currently used for universal vaccination in combination or separately, wherein the priming step occurs before inoculating with the Covid vaccine.

In one or more embodiments, the present invention further comprises a cell in which the recombinant vector is introduced; and a vaccine composition or medicament for treating and/or preventing COVID-19 comprising the recombinant vector; and a method of treating by administering the vector encoding a SARS-CoV receptor binding domain (RBD) gene and a DrTeNT-CoV2 gene to express a RBD and DrTeNT-CoV2 hybrid protein (RBD attached to DrTent-CoV2 protein) in vivo.

In one or more embodiments, the present invention comprises one or more vaccine vehicles able to directly activate memory cells for the processing of the vaccine, and without necessarily alerting the entire immune system for any dire immune response.

In one or more embodiments, the antigen presenting cells (APCs) are able to process the epitopes derived from the S (spike) or N (Nucleocapsid) or M (Membrane) or E (envelope) proteins of SARS-CoV-2, which allows for a more effective and/or a faster immune response against the pathogen (e.g., Covid-19).

In one or more embodiments, the composition is administered comprising the DrTeNT protein or gene as a hybrid or embedded form with a pathogen epitope (or SARS-CoV2), or co-administered as separate proteins or genes. The gene clone of DrTeNT has been used to insert DNA sequences corresponding to the most suitable epitopes of SAR-CoV-2 virus. The resultant combo vaccine is to have higher efficacy for DrTeNT acts as adjuvant, and higher safety as most of the population preimmunized with tetanus vaccine.

BRIEF DESCRIPTION OF THE DRAWINGS

Figure 1:
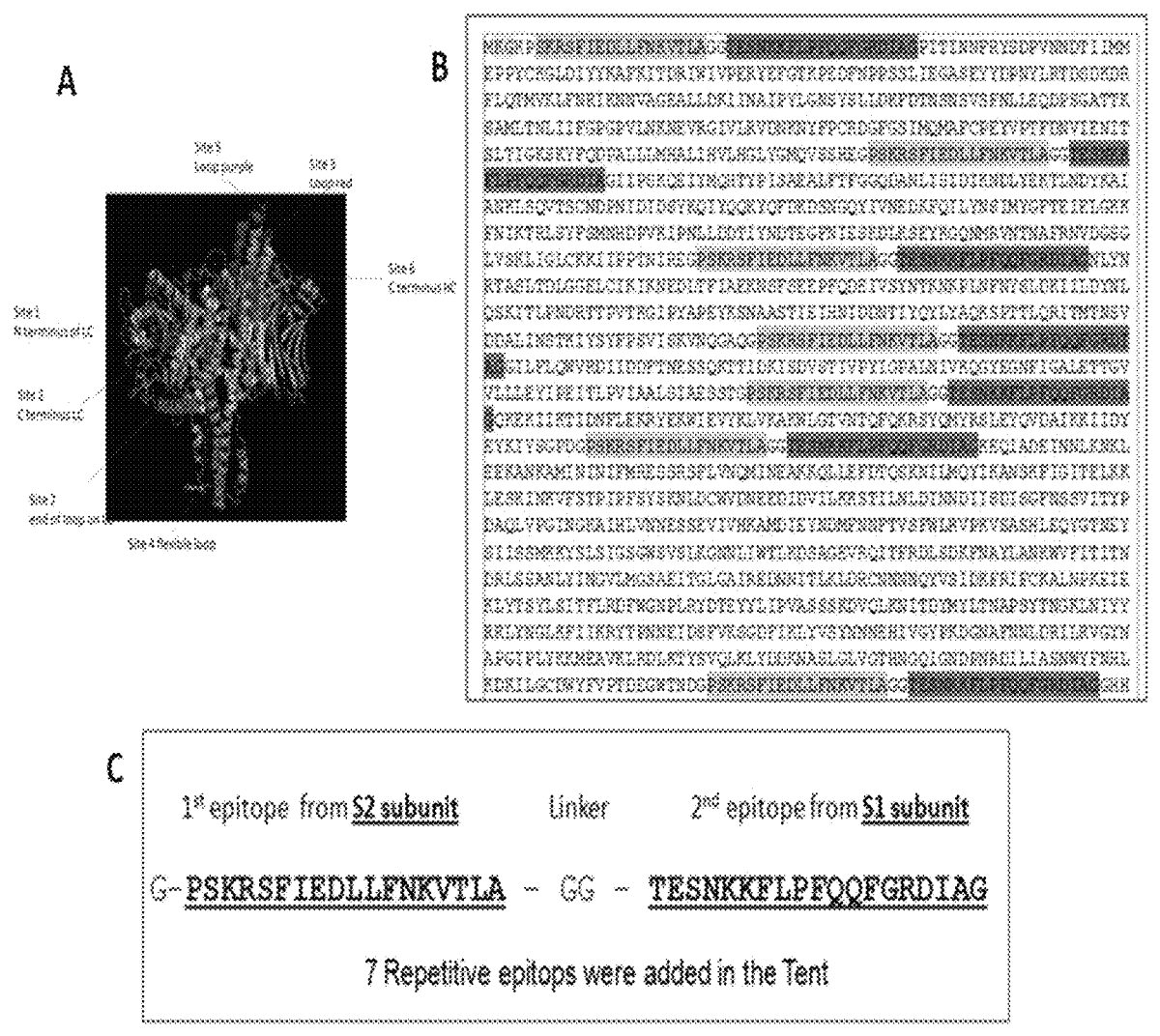

FIG. 1 illustrates the following: "A" shows different sites of DrTeNT where selected epitopes are embedded in DrTeNT-CoV2 (TC2) vaccine; "B" discloses sequences of TC2 (SEQ ID NO: 6); and "C" displays embedded epitopes of the sequence of G-SEQ ID NO: 3-GG-SEQ ID NO: 5.

DETAILED DESCRIPTION

Figure 2:
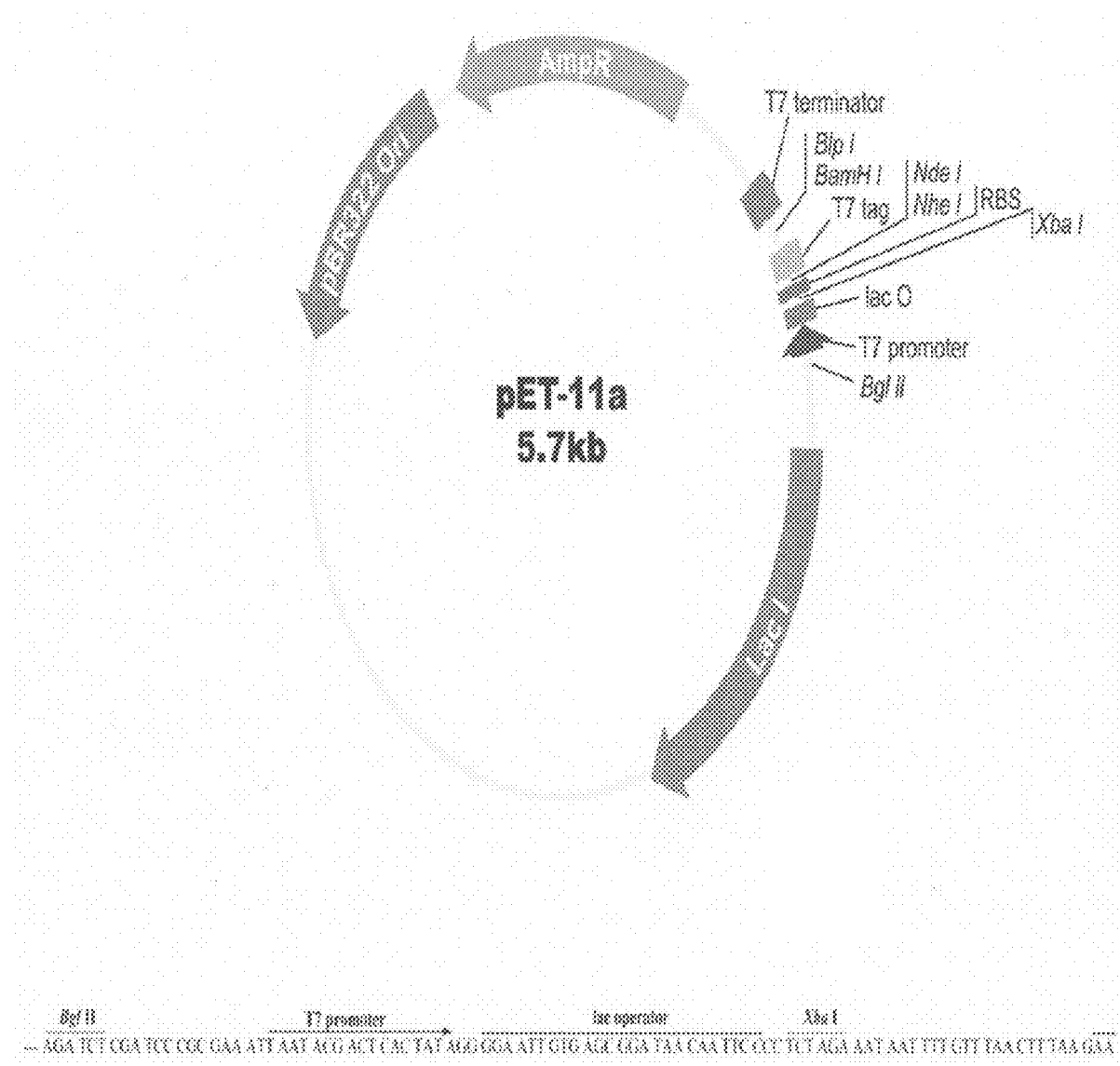
FIG. 2: illustrates a PET-11a vector in which either TC2 or RBD were cloned to express these proteins.

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

Oral or Intranasal Vaccine Delivery

Availability of an oral delivery system (Singh, "Composition for Oral or Nasal Delivery of Tetanus, Diphtheria, and Pertussis Vaccine alone or in combination using Neurotoxin Associated Proteins", United States Patent application number 20190076518 A1 that published Mar. 14, 2019, which is incorporated herein by reference in its entirety) would facilitate the vaccination schemes for pregnant women, infants and the world population in general. The same technology can be incorporated to deliver DrTeNT-CoV2 vaccine or any other vaccine on the DrTeNT platform to be implemented under this invention. Currently, no such vaccine delivery system is available, nor is any effort known to be underway in this direction against COVID-19.

The present invention comprises the utility of DrTeNT-CoV2 as a vaccine candidate, which includes DrTeNT-CoV2 (in which selected epitopes embedded into DrTeNT sequence), DrTeNT-RBD, DrTeNT-S1 or DrTeNT-CoV2 hybrid (RBD or S1 chemically attached to the DrTeNT-CoV2).

The oral/sublingual or intranasal delivery of DrTeNT or DrTeNT-CoV2 is proposed to be facilitated by neurotoxin associated proteins or NAPs produced by *Clostridium botulinum*, an organism that is related to *C. tetani*. Using NAPs as a formulating agent to protect the recombinant protein vaccines can solve the problem of digestive condition in the oral cavity harsh digestive conditions in the stomach, like very low pH and bile acid, and proteases. Further, with the present invention, NAPs protect DrTeNT-CoV2 protein from mucosal, digestive and intestinal unfriendly environment and enzymes, and facilitate the vaccine to evoke the immune response. NAPs will also act as an adjuvant to enhance the immune response. Additionally, NAPs are well known as a transport proteins to help molecules cross the epithelial barrier (12-15), which allows for the delivery of the vaccine sublingually or intranasally. This newly developed vaccine also solves the problem of safety and administration concerns related to the injection of vaccines, because the present invention facilitates oral delivery.

The present invention employs the use of non-toxic neurotoxin associated proteins (NAPs) of botulinum neurotoxin (BoNT) produced by *Clostridium botulinum* as a formulating agent for oral delivery of DrTeNT-CoV2 vaccine. NAPs bind with DrTeNT-CoV2 and its role include formulating agent, protectant, transport protein and an adjuvant.

An oral/sublingual/nasal delivery system for the COVID-19 vaccine will facilitate convenient immunization regime especially for infants, particularly in countries where access to clinics is limited. An oral/sublingual/nasal delivery method for administration of COVID-19 vaccine will be less painful, and safer. There will be no issue of contaminated needles. Currently many vaccines cannot be delivered by oral route because of the harsh digestive conditions (from mouth to intestines) like very low pH, bile acid, and proteases. Moreover, several safety concerns related to the injectable vaccines, e.g., allergic reaction and/or secondary infection.

Thus, the present strategy of using NAPs of botulinum neurotoxin for oral/sublingual/nasal delivery of SARS-CoV-2 vaccine is quite innovative and practical. Oral/sublingual/nasal delivery offers a number of significant advantages over other routes of administration. Oral vaccines are cheaper to administer since they can be delivered outside of a formal clinical setting, without the need for trained personnel. Elimination of needles from the vaccination process can alleviate concerns regarding the reuse and disposal of needles, which has been shown to be responsible for a number of vaccination-related infections. However, oral vaccination has been regarded historically as likely to be less effective, as vaccine antigens undergo digestion in the digestive/GI tract prior to induction of an immune response. NAPs can be employed to address some of these concerns, as these are well known to resist digestion in the GI tract, and are in fact known to help translocate the cargo across the epithelial layer of the gut (13). In fact, certain isolated components of the NAPs have been demonstrated to play a critical role in the protection and translocation process (16, 17), which can be exploited to develop a cleaner oral delivery system using only those isolated components. At present, there are a limited number of oral vaccines approved for human use, but more are in the late stages of clinical development (oral cholera vaccines, typhoid vaccine, tuberculosis, etc.) (18-21). Majority of vaccines are acid labile and need to be administered in a formulation which protects them from acids of GI tract. In the case of cholera oral vaccine, it is formulated in a bicarbonate buffer to protect the vaccine. But it has been reported that such buffers are not well tolerated by some of those taking such vaccine formulation, as it causes adverse GI symptoms such as bloating, gas, cramps, and diarrhea (22).

The SARS-CoV-2 virus carries RNA as their genetic material, and is one of the longest (27 to 32 kb) known viral RNA genome. The structural proteins of SARS-CoV2 include the surface spike glycoprotein (S), the membrane protein (M), the envelope glycoprotein (E), and the nucleocapsid protein (N). These four structural proteins are essential for virion assembly (23).

The spike (S) protein projects through the viral envelope and forms the characteristic spikes in the coronavirus under cryo-electron microscope looks like "crown" (PBD-6VSB) (24). It is heavily glycosylated. The spike (S) glycoprotein of coronaviruses is known to be essential in the binding of the virus to the host cell at the advent of the infection process. The "S" protein is a homotrimer; and it is the sole viral membrane protein responsible for cell entry. It binds to the receptor on the target cell and mediates subsequent virus-cell fusion; hence it is the key target for vaccine design. Because of the dual role (i.e. host receptor recognition, and virus attachment and entry) of S protein, it is a formidable target for the development of the antidote or the vaccine against the SARS-CoV-2.

Tetanus Based Vaccine

The SARS-CoV spike (S) protein is composed of two subunits S1 and S2 proteins; the S1 subunit contains a receptor-binding domain (RBD) that engages with the host cell receptor angiotensin-converting enzyme 2 (ACE2); and the S2 subunit mediates fusion of the viral and host cell membranes. Human proteases cut the spike proteins at specific sites, which leads to the confirmational changes in SARS-CoV2 and facilitates binding to the ACE2 receptor (24). The protease-mediated entry facilitated a 100- to 1,000-fold higher efficient infection than the endosomal pathway used in the absence of protease (25). Proteolytic cleavage of the SARS-CoV-2 spike protein is important for cell-cell fusion and/or virus entry. The different proteases are involved in the cleavage of SARS-CoV-2 spike protein and their roles in activating cell-cell fusion and/or virus entry. There are many studies carried out identifying the various epitopes present on the different proteins on the SARS-CoV-2 (26-29). We believe the N terminus-PSKRSFIELDLLFNKVTLA-C terminus (SEQ ID NO: 3) terminus would be a better target on the surface of S protein.

Recently crystal structural (PDB-6VW1) of RBD (S1) domain binding directly to the ACE2 receptor has published (30, 31). When the SARS-CoV-2 protein binds to ACE2 receptor, all three RBD shifts in the less stable "up" conformation (30). Looking closely at the binding of RBD sequence 481-505 NGVEGFNCYFPLQSYGFQPTNGVGY (SEQ ID NO: 4) and Sequence TESNKKFLPFQQFGRDIAG (SEQ ID NO: 5). The final epitopes would be created by linking one or more of these sequences together.

SEQ ID NO: 2 and 3 have been selected as the possible epitope to design the vaccine against the SARS-CoV-2. Most of the studies identified only 20 or so amino acid residues. The small peptide alone could not elicit the enough immune response when inserted alone. Synthetic small peptide-based vaccines containing immunogenic epitope are able to exceed the antibody titers when combined with the formulating agent like DrTeNT. We predicted multiple epitopes from all the SARS-CoV-2 proteins (Table 3) using SVMTriP software developed by University of Nebraska-Lincoln (32) that can also be considered from embedded sequence in the formulating agent DrTeNT. The concept of exceeding the immune response using DrTeNT as a carrier protein (or vector) is not limited to the selected epitope (Table 2) but can be used with other epitopes of SARS-CoV-2 virus listed in Table 3.

Following constructs are part of this technology:
1) Epitopes embedded into DrTeNT sequence (Vaccine 1);
2) Modified epitopes (at least 85% sequence similarity of SEQ ID NOS: 3-5, and/or Table 1) embedded into DrTeNT sequence (Vaccine 2);
3) RBD or S1 attached to the DrTeNT sequence using molecular biology techniques (Vaccine 3);
4) RBD or S1 attached chemically to DrTeNT sequence (Vaccine 4); and
5) RBD or S1 attached chemically to V1 (Vaccine 5).

Details of the Vaccine Technology for Creating Oral COVID Vaccine

Seven different sites of the DrTENT proteins have been selected using software SVMTrip™: A tool to predict linear antigenic epitopes, developed by the University of Nebraska-Lincoln, was used to selected possible immunogenic sites. Seven different sites have used to insert the combined epitopes from S1 and S2 subunit of the SARS-CoV-2 proteins. These epitopes were attached with the di-glycine (GG) linker for the additional flexibility. The created DrTeNT protein with epitopes (selected from the SARS-CoV-2 protein S1 domain) embedded in it is called DrTeNT-CoV-2 (TC-2; SEQ ID NO: 6). The epitopes are selected from S1 and S2 subunits for the SARS-CoV-2 proteins that were mentioned as SEQ ID NOS: 3-5, and in Table 1. Hybrid chimeric protein (SEQ ID NO: 7) was created by covalently adding RBD (SEQ ID NO: 2) to TC-2 sequence (SEQ ID NO: 6).

TABLE 1

List of the predicted epitopes of the SARS-CoV-2 virus.

| SEQ ID NO. | SARS-CoV-2 proteins | Location | Epitope | Score |
| --- | --- | --- | --- | --- |
| 8 | S | 1186-1205 | LNEVAKNLNESLIDLQELGK | 1 |
| 9 | S | 961-980 | TLVKQLSSNFGAISSVLNDI | 0.987 |
| 10 | S | 1010-1029 | QQLIRAAEIRASANLAATKM | 0.963 |
| 11 | S | 1149-1168 | KEELDKYFKNHTSPDVDLGD | 0.961 |
| 12 | S | 1228-1247 | VMVTIMLCCMTSCCSCLKGC | 0.827 |
| 13 | S | 740-759 | MYICGDSTECSNLLLQYGSF | 0.701 |
| 14 | S | 882-901 | ITSGWTFGAGAALQIPFAMQ | 0.681 |
| 15 | S | 690-709 | QSIIAYTMSLGAENSVAYSN | 0.509 |
| 16 | S | 571-590 | DTTDAVRDPQTLEILDITPC | 0.466 |
| 17 | S | 595-614 | VSVITPGTNTSNQVAVLYQD | 0.457 |
| 18 | N | 239-258 | QQQQGQTVTKKSAAEASKKP | 1 |
| 19 | N | 276-295 | RRGPEQTQGNFGDQELIRQG | 0.865 |
| 20 | N | 217-236 | AALALLLLDRLNQLESKMSG | 0.676 |
| 21 | N | 186-205 | SSSRSRNSSRNSTPGSSRGT | 0.663 |
| 22 | N | 359-378 | AYKTFPPTEPKKDKKKADE | 0.638 |
| 23 | N | 333-352 | YTGAIKLDDKDPNFKDQVIL | 0.471 |
| 24 | N | 74-93 | INTNSSPDDQIGYYRRATRR | 0.317 |
| 25 | N | 128-147 | DGIIWVATEGALNTPKDHIG | 0.282 |
| 26 | N | 29-48 | NGERSGARSKQRRPQGLPNN | 0.221 |
| 27 | N | 303-322 | QIAQFAPSASAFFGMSRIGM | 0.216 |
| 28 | M | 96-115 | FIASFRLFARTRSMWSFNPE | 1 |
| 29 | M | 151-170 | IAGHHLGRCDIKDLPKEITV | 0.255 |

TABLE 1-continued

List of the predicted epitopes of the SARS-CoV-2 virus.

| SEQ ID NO. | SARS-CoV-2 proteins | Location | Epitope | Score |
|---|---|---|---|---|
| 30 | Orf1ab | 5921-5940 | VATLQAENVTGLFKDCSKVI | 1 |
| 31 | Orf1ab | 2793-2812 | VHVMSKHTDFSSEIIGYKAI | 0.712 |
| 32 | Orf1ab | 3967-3986 | AVANGDSEVVLKKLKKSLNV | 0.691 |
| 33 | Orf1ab | 571-590 | DGISQYSLRLIDAMMFTSDL | 0.651 |
| 34 | Orf1ab | 288-307 | VEKKKLDGFMGRIRSVYPVA | 0.639 |
| 35 | Orf1ab | 5278-5297 | QYIRKLHDELTGHMLDMYSV | 0.618 |
| 36 | Orf1ab | 4023-4042 | AKVTSAMQTMLFTMLRKLDN | 0.612 |
| 37 | Orf1ab | 5703-5722 | ATNYDLSVVNARLRAKHYVY | 0.589 |
| 38 | Orf1ab | 6619-6638 | LIGEAVKTQFNYYKKVDGVV | 0.566 |
| 39 | Orf1ab | 5018-5037 | MPNMLRIMASLVLARKHTTC | 0.565 |
| 40 | Orf3a | 184-203 | YQIGGYTEKWESGVKDCVVL | 1 |
| 41 | Orf3a | 24-43 | TPSDFVRATATIPIQASLPF | 0.563 |
| 42 | Orf3a | 139-158 | LLYDANYFLCWHTNCYDYCI | 0.51 |
| 43 | Orf7a | 70-89 | GVKHVYQLRARSVSPKLFIR | 1 |
| 44 | Orf7a | 14-33 | TCELYHYQECVRGTTVLLKE | 0.921 |
| 45 | Orf8 | 41-60 | FYSKWYIRVGARKSAPLIEL | 1 |
| 46 | Orf8 | 98-117 | LVVRCSFYEDFLEYHDVRVV | 0.7 |

The purification of the TeNT-Cov-2 and RBD (319-541 amino acid) of SARS-Cov-2 protein. DrTeNT-CoV2 gene or RBD gene were inserted in the pET-11a vector between Nde I and Xba I sites. Using previously prepared LB Agar plates with 0.05 mg/mL Carbenicillin, newly transformed DrTeNT-CoV-2 (+) (TC2) plasmid or RBD (+) plasmid BL21DE3 competent cells were spread and incubated at 37° C. overnight. After 14+ hours of growth individual colonies were observed on the plates. These plates were placed at 4° C. and used for growing overnight cultures.

Overnight starter cultures were sterilized 2XYT media with 0.05 mg/mL Carbenicillin added after cooled to room temperature. Several colonies of either TC2 or RBD were grown and after about 12-15 hours, 37° C., 250 rpm. 20 mL of overnight culture was added to 1 Liter of 2XYT media in a 3 L flask, 37° C., 200 rpm. Turbidity was monitored at 600 nm, when the cultures had an absorbance of 0.6-0.8, 1 mM Isopropyl β-D-1-thiogalactopyranoside (IPTG) was added. Then incubated at room temperature (25° C.), 75 rpm for overnight 15 to 17 hours. Cells were pelleted by centrifugation, 4° C., 13,000×g, 20 minutes. Pellets were then kept and frozen at -20° C.

Purification of the newly grown cells were done in 50 mM Tris HCl, pH 8 containing 150 mM sodium chloride. This was kept cold throughout the procedure. Lysis buffer was prepared with this buffer, along with Protease Inhibitor tablet, trace amounts of lysozyme and DNase. The frozen pellet of TC2 or RBD was then suspended in the lysis buffer. This was mechanically sonicated with 3 minutes of processing on cold beads. It was cycled 1 second on/5 seconds off, 18 to 22 watts of peak power. The lysate was centrifuged at 13,000×g, 45 minutes at 4° C.

While centrifuging, 2 mL of fresh nickel agarose beads were equilibrated with the tris buffer in cold chamber. The clarified lysate was then applied to the beads at about 8-14 s/drop in a 1.5 cm×20 cm column. After loading, 10 mL of additional fresh tris was used to wash the beads. Then using imidazole added to the buffer the protein was collected in fractions. TC2 was eluted with varying 20 to 100 mM Imidazole and 250 mM imidazole containing buffer, pH8, where the majority of the pure product was in the 250 mM eluent. RBD was eluted with several 5 mM imidazole and 10 mM imidazole to capture the purest product. Higher imidazole did elute protein but there was a greater amount of non-target material mixed with the RBD.

Figure 3:
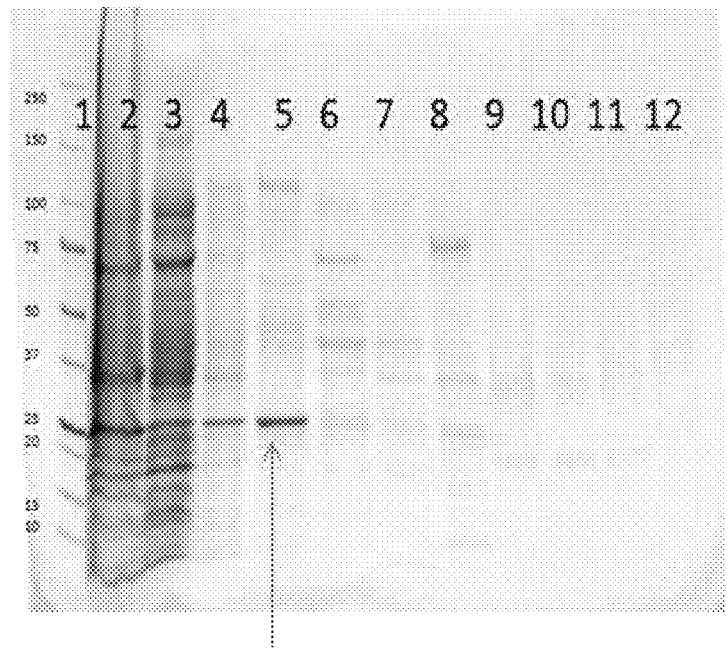
FIG. 3: illustrates a western blot, where the lanes represent the purification of RBD protein from SARS-CoV-2. Lane 1 is the molecular weight marker; Lane 2 is the Lysate from cells; Lane 3 is the flow through from column; Lane 4 is 5 mM imidazole; Lane 5 is 20 mM imidazole; Lanes 6-7 are 50 mM imidazole; Lane 8 is 100 mM imidazole; Lanes 11-12 are 200 mM imidazole. The major bands for RBD were observed at 28 kDa and 75 kDa (trimer). This material was further investigated by ELISA.
Figure 4:
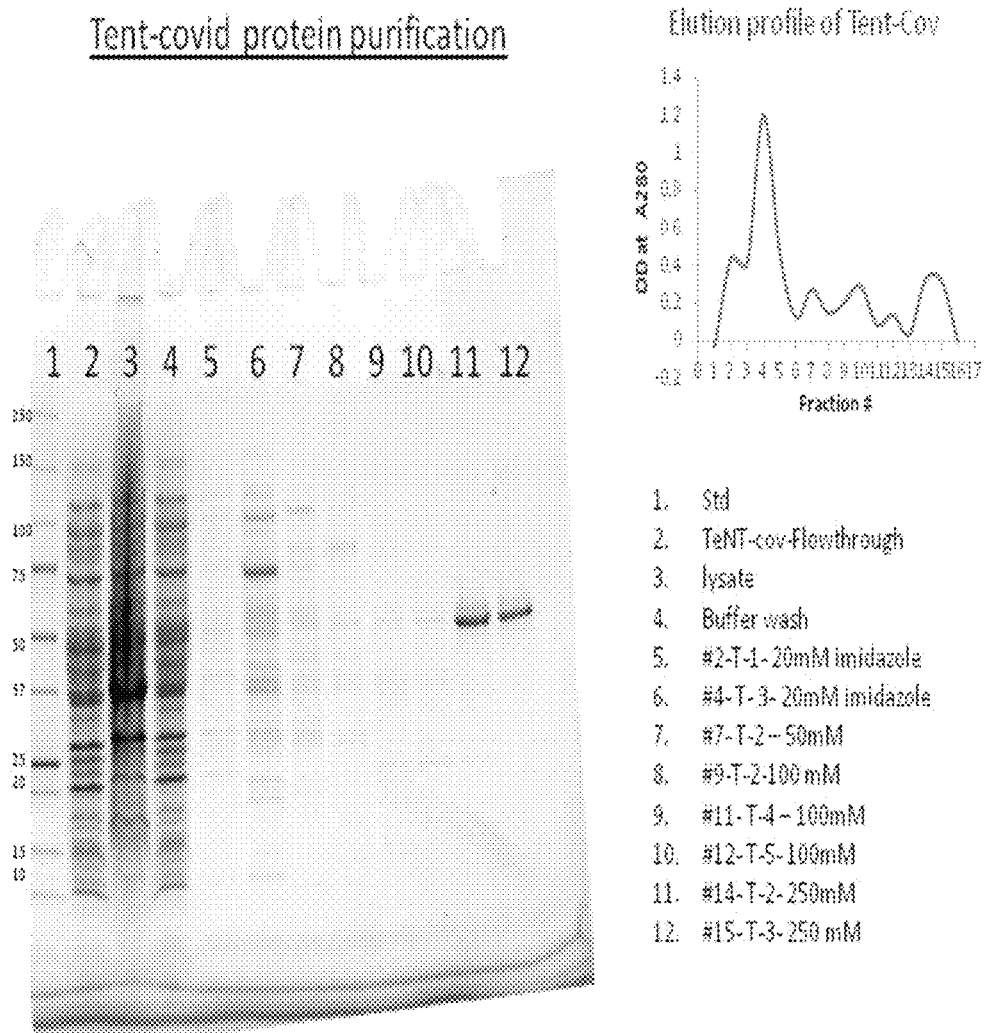
FIG. 4 is a western blot illustrating the purification of the DrTeNT-CoV2 (FIG. 6) protein, and represents as follows: Lane 1 is the molecular weight marker; Lane 2 is the flow through from column; Lane 3 is the lysate from the cells; Lane 4 is the buffer wash; Lanes 5-6 are 20 mM imidazole; Lane 7 is 50 mM imidazole; Lanes 8-10 are 100 mM imidazole; Lanes 11-12 are 250 mM imidazole. The major bands for TC2 were observed 50 kDa.

Samples were measured by UV/VIS spectrophotometer and protein was estimated by using absorbance data as follows: $(A_{235nm}-A_{280nm})/2.51=\sim 0.66$ mg/ml of DrTeNT-CoV2 and 0.3 mg/ml of RBD. Proteins were stored with 20% added glycerol and flash frozen and stored at least -20° C. Sample purity was monitored by SDS-PAGE electrophoresis (FIGS. 3 and 4).

Creation of the Hybrid Protein by Combining TC2 and RBD by EDC Crosslinking to the Sulfo-NHS Using Two-Step Linking.

Figure 5:
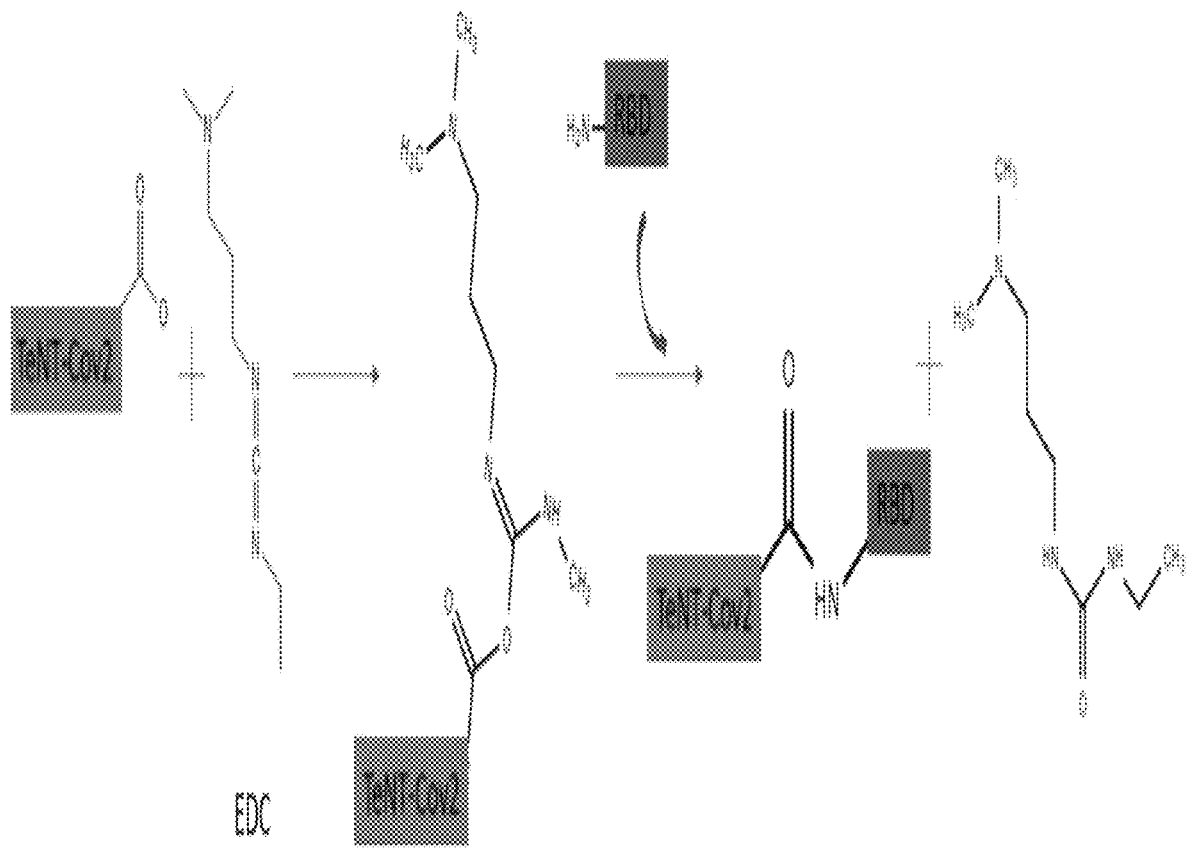
FIG. 5 illustrates the chemical linking of TC2 and RBD using EDC to produce hybrid protein.
Figure 6:
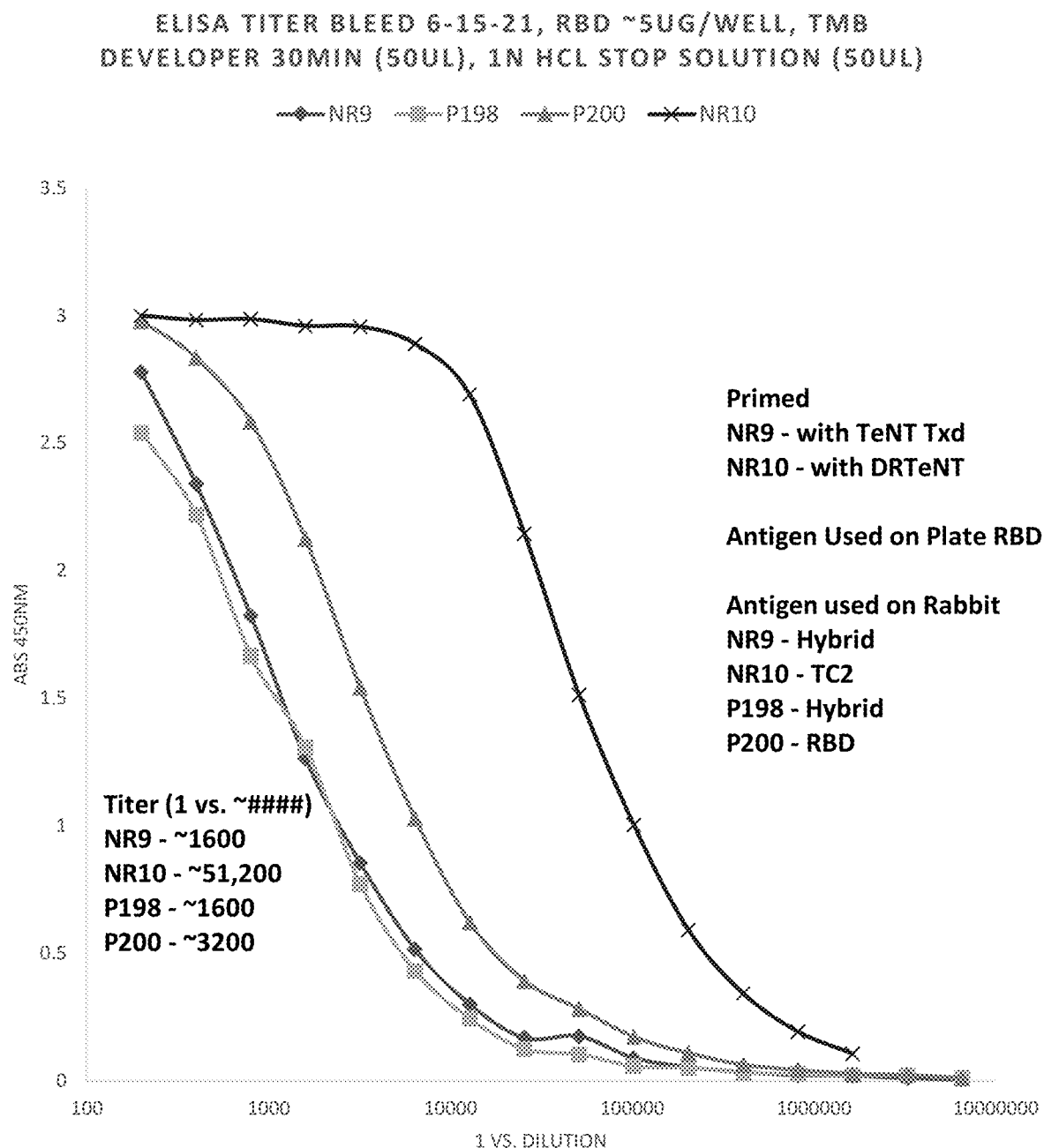
FIG. 6 is an ELISA titer graph of RBD, TC2 and hybrid protein before and after DrTeNT priming in the rabbit.

EDC is the cross linker used for the linking RBD of SARS-CoV-2 with the DrTeNT-CoV2 (TC2) to create the hybrid protein (FIG. 5). EDC and Sulfo-NHS allows two-step coupling of the both the proteins without affecting the carboxyls of the second proteins. EDC activates carboxyl groups and spontaneously reacts with primary amines to form an amide bond. EDC couples NHS to carboxyl, which forms an NHS ester and allows for efficient conjugation to primary amines at physiologic pH. The EDC and NHS were equilibrated at room temperature. 1 mg/ml of DrTeNT-CoV2 (TC2) solution in conjugation buffer. 0.4 mg EDC and 1.1 mg sulfo-NHS were mixed and incubated for 15 min at room temperature. 1.2 μl 2-mercaptoethanol was added to the mixture to quench the EDC reaction. RBD protein was added to in the reaction mixture and incubated for 2 hours at room temperature. The reaction was quenched by adding hydroxylamine. Thus, the Hybrid protein was created by attaching DrTeNT-CoV2 (TC2) to RBD protein (SEQ ID NO: 7).

Immune Response in Rabbit

Rabbits were exposed to Tetanus toxoid and DrTeNT three months prior to the exposure them with the TC2, Hybrid and RBD proteins. The primed and unprimed rabbits were exposed to same 7 μg of the all three proteins TC2, RBD and hybrid. The serum from the rabbit was collected after 3 months to check the immune response using ELISA.

Antigen was prepared for coating the plates. 5 μg/well of RBD antigen was used in Phosphate Buffered Saline (PBS). Similar plates were also prepared in this manner with TeNT-CoVid Hybrid antigen using 5 ug/well in PBS. This was incubated at 4° C. for 15 hours. The wells were blocked using 3% Bovine Serum Albumin (BSA) in PBS, 0.2 mL/well. This was blocked at 37° C. for 1 hour. The plates were washed 3 times using PBS+0.05% Tween 20 (PBST), 0.3 mL/well/wash for 3 to 5 minutes.

After washing, the plates were blotted onto clean paper towels until wells were dry. Next 3% BSA in PBS, 0.1 mL was added to all the wells. A series of dilutions were done with the sera from the 6-15-21 bleeds.

Rabbits NR9, NR10, P198 and P200 were tested. Similar dilutions were done against the DrTeNT-Covid Hybrid (Hybrid) antigen protein; the rabbits used for that ELISA were NR9, NR10, P198 and P199. The sera dilutions were allowed to incubate 1 to 3 hours at 37° C. The dilutions started at 1:200 and were double diluted to ~1:6 million. The plates were washed with PBST, as before.

Secondary antibody was prepared by adding commercially purchased goat anti-rabbit peroxidase conjugated IgG antibodies. 1:10,000 dilution into 3% BSA in PBS. 0.1 mL/well, 1 hour, 37° C. Plates were washed again, as before and blotted to dryness on clean paper towels.

The Plates were then developed by peroxidase reactive developer that was monitored by Thermomax plate reader. Reactions were then read at 450 nm to obtain readings and results were plotted to give results. The results suggest that the rabbits primed with DrTeNT showed highest immune response against Covid epitopes imbedded in DrTeNT. This was nearly 32-fold higher than unprimed vaccination and 16-fold higher than the RBD vaccination.

Conclusion

It will be appreciated that the methods and compositions of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Or, the technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed.

The term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 5%), and use of the term "about" at the beginning of a string of values modifies each of the values. As used herein, the term "substantially" refers to approximately the same shape as stated.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments.

Trademarks: the product names used in this document are for identification purposes only; and are the property of their respective owners.

LIST OF REFERENCES CITED

1. Thanh Le T, Andreadakis Z, Kumar A, Gomez Roman R, Tollefsen S, Saville M, Mayhew S. 2020. The COVID-19 vaccine development landscape. Nat Rev Drug Discov 19:305-306.
2. Hotez P J, Bottazzi M E, Corry D B. 2020. The potential role of Th17 immune responses in coronavirus immunopathology and vaccine-induced immune enhancement. Microbes Infect doi:10.1016/j.micinf.2020.04.005.
3. Smatti M K, Al Thani A A, Yassine H M. 2018. Viral-Induced Enhanced Disease Illness. Front Microbiol 9:2991.
4. Konig M F, Powell M A, Staedtke V, Bai R-Y, Thomas D L, Fischer N M, Huq S, Khalafallah A M, Koenecke A, Xiong R, Mensh B, Papadopoulos N, Kinzler K W, Vogelstein B, Vogelstein J T, Athey S, Zhou S, Bettegowda C. 2020. Preventing cytokine storm syndrome in COVID-19 using α-1 adrenergic receptor antagonists. J Clin Invest doi:10.1172/jci139642.
5. Mehta P, McAuley D F, Brown M, Sanchez E, Tattersall R S, Manson J J, Hlh Across Specialty Collaboration UK. 2020. COVID-19: consider cytokine storm syndromes and immunosuppression. Lancet 395:1033-1034.
6. Jose R J, Manuel A. 2020. COVID-19 cytokine storm: the interplay between inflammation and coagulation. Lancet Respir Med.
7. Deinhardt K, Schiavo G. 2005. Endocytosis and retrograde axonal traffic in motor neurons. Biochem Soc Symp:139-50.
8. Schiavo G, Rossetto O, Santucci A, DasGupta B R, Montecucco C. 1992. Botulinum neurotoxins are zinc proteins. J Biol Chem 267:23479-83.
9. Lacy D B, Stevens R C. 1999. Sequence homology and structural analysis of the clostridial neurotoxins. J Mol Biol 291:1091-104.
10. Singh B R, Chang T-W, Kukreja R, Cai S. 2014. The Botulinum Neurotoxin Complex and the Role of Ancillary Proteins, p 69-101. In Foster K A (ed), Molecular Aspects of Botulinum Neurotoxin. Springer New York, New York, N.Y.
11. Schiavo G, Matteoli M, Montecucco C. 2000. Neurotoxins affecting neuroexocytosis. Physiol Rev 80:717-66.
12. Ravichandran E, Janardhanan P, Patel K, Riding S, Cai S, Singh B R. 2016. In Vivo Toxicity and Immunological Characterization of Detoxified Recombinant Botulinum Neurotoxin Type A. Pharm Res 33:639-52.
13. Ghosal K J, Patel K, Singh B R, Hale M L. 2018. Role of critical elements in botulinum neurotoxin complex in toxin routing across intestinal and bronchial barriers. PLoS One 13:e0199524.
14. Cai S, Ramsamooj N, Patel K, Kumar R, Singh B R. BoNT NAPs for oral delivery of protein drugs and vaccines, p. In (ed),
15. Cai S, Ramsamooj N, Patel K, Kumar R, Singh B R. 2019. Botulinum Neurotoxin Associate Proteins for Oral Delivery of Protein Drugs and Vaccine, abstr The Interagency Botulism Research Coordinating Committee (IBRCC) meeting
16. Williams G A, Koenen M E, Havenaar R, Wheeler P, Gowtage S, Lesellier S, Chambers M A. 2019. Survival of *Mycobacterium bovis* BCG oral vaccine during transit through a dynamic in vitro model simulating the upper gastrointestinal tract of badgers. PLoS One 14:e0214859.
17. Sanchez J L, Trofa A F, Taylor D N, Kuschner R A, DeFraites R F, Craig S C, Rao M R, Clemens J D, Svennerholm A M, Sadoff J C, et al. 1993. Safety and 18. Kumar R, Chang, T. W., and Singh, B. R. 2017. Evolutionary traits of toxins. Springer Netherlands.
19. Singh B R, Li B, Read D. 1995. Botulinum versus tetanus neurotoxins: why is botulinum neurotoxin but not tetanus neurotoxin a food poison? Toxicon 33:1541-7.
20. Yang W, Lindo P, Riding S, Chang T W, Cai S, Van T, Kukreja R, Zhou Y, Vasa K, Singh B R. 2008. Expression, purification and comparative characterisation of enzymatically deactivated recombinant botulinum neurotoxin type A. The Botulinum journal 1:219-241.
21. Sakaguchi G. 1982. *Clostridium botulinum* toxins. Pharmacol Ther 19:165-94.
22. Costantino H R, Schwendeman S P, Griebenow K, Klibanov A M, Langer R. 1996. The secondary structure and aggregation of lyophilized tetanus toxoid. J Pharm Sci 85:1290-3.
23. Belouzard S, Millet J K, Licitra B N, Whittaker G R. 2012. Mechanisms of coronavirus cell entry mediated by the viral spike protein. Viruses 4:1011-33.
24. Wrapp D, Wang N, Corbett K S, Goldsmith J A, Hsieh C L, Abiona O, Graham B S, McLellan J S. 2020. Cryo-EM structure of the 2019-nCoV spike in the prefusion conformation. Science 367:1260-1263.
25. Matsuyama S, Ujike M, Morikawa S, Tashiro M, Taguchi F. 2005. Protease-mediated enhancement of severe acute respiratory syndrome coronavirus infection. Proc Natl Acad Sci USA 102:12543-7.
26. Robson B. 2020. COVID-19 Coronavirus spike protein analysis for synthetic vaccines, a peptidomimetic antagonist, and therapeutic drugs, and analysis of a proposed achilles' heel conserved region to minimize probability of escape mutations and drug resistance. Comput Biol Med doi:10.1016/j.compbiomed.2020.103749:103749.
27. Robson B. 2020. Computers and viral diseases. Preliminary bioinformatics studies on the design of a synthetic vaccine and a preventative peptidomimetic antagonist against the SARS-CoV-2 (2019-nCoV, COVID-19) coronavirus. Comput Biol Med 119:103670.
28. Grifoni A, Sidney J, Zhang Y, Scheuermann R H, Peters B, Sette A. 2020. Candidate targets for immune responses to 2019-Novel Coronavirus (nCoV): sequence homology- and bioinformatic-based predictions.
29. Ahmed S F, Quadeer A A, McKay M R. 2020. Preliminary Identification of Potential Vaccine Targets for the COVID-19 Coronavirus (SARS-CoV-2) Based on SARS-CoV Immunological Studies. Viruses 12.
30. Shang J, Ye G, Shi K, Wan Y, Luo C, Aihara H, Geng Q, Auerbach A, Li F. 2020. Structural basis of receptor recognition by SARS-CoV-2.
31. Yan R, Zhang Y, Li Y, Xia L, Guo Y, Zhou Q. 2020. Structural basis for the recognition of SARS-CoV-2 by full-length human ACE2. Science 367:1444-1448.
32. Yao B, Zhang L, Liang S, Zhang C. 2012. SVMTriP: a method to predict antigenic epitopes using support vector machine to integrate tri-peptide similarity and propensity. PLoS One 7:e45152.
33. United States Patent application number 20190076518 A1 that published March 14,

What is claimed is:

1. A recombinant or a conjugate protein vaccine composition for treating or preventing a COVID-19 infection, comprising:
   a) one or more proteins, or a variant thereof, comprising detoxified forms of a tetanus neurotoxin (DrTeNT);
   b) wherein the one or more proteins, or the variant thereof, are embedded with or chemically attached to one or more epitopes and/or domains encoding a targeted immunogenic peptide derived from a Severe Acute Respiratory Syndrome (SARS-COV2) disease or a variant thereof, to create a Tetanus COVID (TC2) recombinant protein vaccine, or a TC2 or DrTeNT conjugate protein vaccine;
   c) wherein said recombinant or conjugate protein vaccine composition comprises the one or more proteins having at least 90% sequence identity to the full length of SEQ ID NOS: 6 or 7; and
   d) wherein said recombinant or conjugate protein vaccine composition is able to activate memory cells against Severe Acute Respiratory Syndrome (SARS-COV2) without an adverse immune response while excluding formaldehyde.

2. The vaccine composition of claim 1, wherein the conjugate protein vaccine comprises chemically attaching the one or more DrTeNT or TC2 or any variant thereof to the one or more epitopes and/or domains comprising a receptor binding domain (RBD) and/or a S1 domain and/or a S2 domain of the SARS-COV2 to create a hybrid protein.

3. The vaccine composition of claim 1, wherein the vaccine is a recombinant protein vaccine.

4. The vaccine composition of claim 1, wherein the vaccine composition is able to immunize a human or a non-human mammal against SARS -CoV2 infection.

5. The vaccine composition of claim 1, wherein the disease encodes a targeted protein comprising S1 and RBD epitopes that are derived from the SARS-COV2virus as a source material.

6. The vaccine composition of claim 1, further comprises a second vaccine composition wherein the epitopes are derived from one or more pathogen proteins associated with viral diseases comprising: flu, dengue, HIV, and variants thereof.

7. The vaccine composition of claim 1, wherein the detoxified form of the vaccines contains one or more modifications comprising deletions, insertions, or substitutions of nucleotide or amino acid sequences in the embedded SARS-COV2epitopes.

8. The vaccine composition of claim 1, further comprising a formulating agent for oral, sublingual, and/or nasal delivery by adding one or more neurotoxin associated proteins (NAPs) derived from a botulinum neurotoxin (BoNT) produced by a *Clostridium*.

9. The vaccine composition of claim 1, further comprising an adjuvant comprising one or more of: alum, polylactic acid, polyglycolic acid, Vitamin E, and colloidal particle.

10. The vaccine composition of claim 1, comprising at least 90% sequence identity to one or more of SEQ ID NOS: 3, 5.

11. The vaccine composition of claim 1, comprising at least 90% sequence identity to SEQ ID NO: 6.

12. The vaccine composition of claim 1, wherein the inserted epitopes are between $^4$K and $^{44}$P; $^{294}$G and $^{334}$G; $^{533}$G and $^{573}$N; $^{731}$G and $^{771}$G; $^{858}$G and $^{898}$Q; $^{970}$G and $^{1010}$K of SEQ ID NO: 6.

13. The vaccine composition of claim 2, wherein DrTeNT is attached chemically to the one or more epitopes and/or domains comprising the receptor binding domain (RBD) and the S1 domain and the S2 domain of the SARS-COV2 to create a hybrid protein.

14. The vaccine composition of claim 13, comprising at least 90% sequence identity to SEQ ID NO: 7.

\* \* \* \* \*